(12) United States Patent
Rong et al.

(10) Patent No.: US 9,771,343 B2
(45) Date of Patent: *Sep. 26, 2017

(54) 2-ALKYL-OR-ARYL-SUBSTITUTED TANSHINONE DERIVATIVES, AND PREPARATION METHOD AND APPLICATION THEREOF

(71) Applicant: Hangzhou Bensheng Pharmaceutical Co., Ltd., Zhejiang (CN)

(72) Inventors: Frank Rong, Zhejiang (CN); Rongzhen Xu, Zhejiang (CN); Fuwen Xie, Fujian (CN); Hongxi Lai, Fujian (CN)

(73) Assignee: HANGZHOU BENSHENG PHARMACEUTICAL CO., LTD., Hangzhou, Zhejiang (CN)

(*) Notice: Subject to any disclaimer, the term of this patent is extended or adjusted under 35 U.S.C. 154(b) by 39 days.

This patent is subject to a terminal disclaimer.

(21) Appl. No.: 14/361,533

(22) PCT Filed: Nov. 30, 2012

(86) PCT No.: PCT/CN2012/085649
§ 371 (c)(1),
(2) Date: May 29, 2014

(87) PCT Pub. No.: WO2013/079017
PCT Pub. Date: Jun. 6, 2013

(65) Prior Publication Data
US 2014/0336249 A1    Nov. 13, 2014

(30) Foreign Application Priority Data
Nov. 30, 2011 (CN) .................. PCT/CN2011/083256

(51) Int. Cl.
*C07D 307/87* (2006.01)
*C07J 75/00* (2006.01)
*C07J 73/00* (2006.01)
*A61K 31/56* (2006.01)
*C07D 307/77* (2006.01)

(52) U.S. Cl.
CPC ............ *C07D 307/87* (2013.01); *A61K 31/56* (2013.01); *C07D 307/77* (2013.01); *C07J 73/003* (2013.01); *C07J 75/00* (2013.01)

(58) Field of Classification Search
CPC ....... C07J 73/003; C07J 75/00; C07D 307/77; C07D 307/87; A61K 31/56
See application file for complete search history.

(56) References Cited

U.S. PATENT DOCUMENTS 9,328,083 B2    5/2016   Xu et al.
2007/0207989 A1  9/2007   Dev et al.

FOREIGN PATENT DOCUMENTS

| CN | 1837199 | * | 9/2006 |
| CN | 1837200 A | | 9/2006 |
| CN | 101012270 A | | 8/2007 |
| WO | WO 2009/084834 | * | 7/2009 |
| WO | 2013/079022 A1 | | 6/2013 |

OTHER PUBLICATIONS

Luo et al., "Relationship between structure and antibacterial activities of tanshinones and related compounds". Zhongguo Yaoke Daxue Xuebao, vol. 19(4), 258-262, 1988. English translation.*
Yang et al. 'Modification of Diterpenoid Quinones from Salvia miltiorrhiza'. Journal of China Pharmaceutical University. 1998, vol. 29, No. 4, pp. 255-258, English Abstract only.
Luo et al. 'Relationship Between Structure and Antibacterial Activities of Tanshinones and Related Compounds'. Journal of China Pharmaceutical University. 1988, vol. 19, No. 4, pp. 258-262, English Abstract only.
International Search Report as it relates to International Patent Application No. PCT/CN2012/085649, dated Feb. 2013. (5 pages).
International Preliminary Report on Patentability as it relates to International Patent Application No. PCT/CN2012/085649, dated Jun. 3, 2014. (11 pages).

(Continued)

*Primary Examiner* — Barbara P Badio
(74) *Attorney, Agent, or Firm* — Brian C. Trinque; Lathrop & Gage LLP

(57) ABSTRACT

The present invention belongs to the field of natural medicine and pharmaceutical chemistry, and specifically relates to novel 2-alkyl- or 2-aromatic-substituted tanshinone I derivatives of formula (I) or a pharmaceutically acceptable salt thereof, to a process for the preparation of these compounds, compositions containing such compounds and their use in preparing antineoplastic medicaments. When Z=R, said derivative is 2-alkyl-substituted tanshinone I; when Z=Ar, said derivative is 2-aryl-substituted tanshinone I; when Z=Het, said derivative is 2-heteroaryl- or 2-heterocyclyl-substituted tanshinone I.

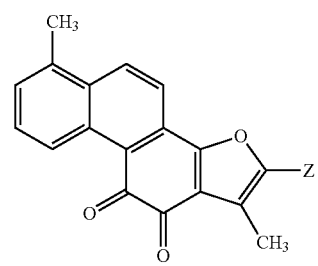

3 Claims, No Drawings

(56) References Cited

OTHER PUBLICATIONS

Shi et al. (2011) "Growth Inhibition of Tanshinones on SPC-A-1 Cell Line and their Structure-activity Relationship," Chin. J. Lung Cancer. 14(1):7-12.—English Abstract only.
Ye et al. (2009) "Inhibition and Structure-Activity Relation of Tanshinones on Growth of HeLa Cell Line," Herald of Medicine 28(10):1261-1264.—English Abstract only.
Sun et al. (1985) "[Synthesis of Some Compounds Related to Tanshinquinone]," Yao Xue Xue Bao. 20(1):39-43.—English abstract, Drawings.

* cited by examiner

2-ALKYL-OR-ARYL-SUBSTITUTED TANSHINONE DERIVATIVES, AND PREPARATION METHOD AND APPLICATION THEREOF

RELATED APPLICATIONS

This application is a 35 U.S.C. §371 filing of International Application No. PCT/CN2012/085649, filed Nov. 30, 2012, which claims priority to International Application No. PCT/CN2011/083256, filed Nov. 30, 2011, each of which is incorporated herein by reference in its entirety.

TECHNICAL FIELD

The present invention belongs to the field of natural medicine and pharmaceutical chemistry, and relates to novel tanshinone derivatives, in particular 2-alkyl- or 2-aromatic-substituted tanshinone I derivatives, to a process for the preparation of these compounds, compositions containing such compounds and their use in preparing antineoplastic medicaments.

BACKGROUND OF THE INVENTION

Tanshinone I, also known as tanshinquinone I, has a chemical formula of 1,6-dimethyl-phenanthreno [1,2-b] furan-10,11-diketone and is extracted from the roots and stems of a Lamiaceae family plant, the *Salvia miltiorrhiza* Bge. Tanshinone I has various pharmacological effects and a wide range of clinical use. It can be used for the treatment of coronary heart disease, angina, myocardial infarction, viral myocarditis, cardiac arrhythmia, cerebral vascular disease, cerebral ischemia, cerebral thrombosis, cerebral infarction, hepatitis, tumor, hypertension and other diseases. Therefore, scientists have conducted a multitude of research on the following tanshinone derivatives.

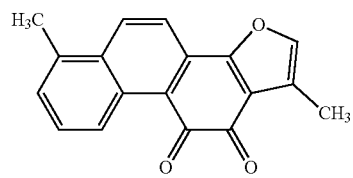

Tanshinone I

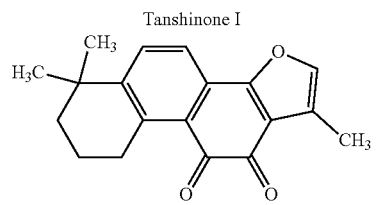

Tanshinone IIA

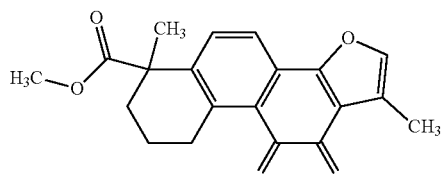

Methyl tanshinonate

-continued

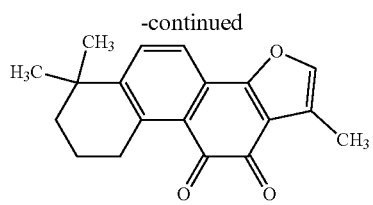

Cryptotanshinone

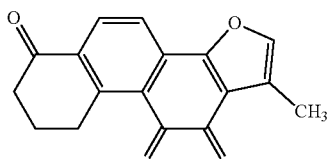

Nortanshinone

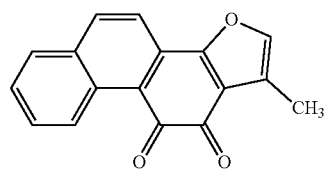

Demethyltanshinone

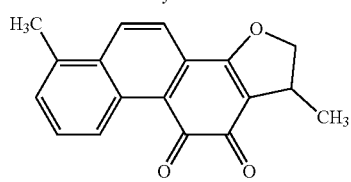

dihydrotanshinone I

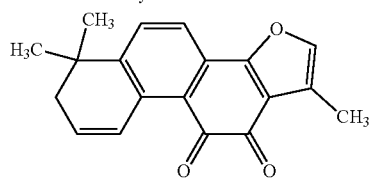

dihydrotanshinone IIA

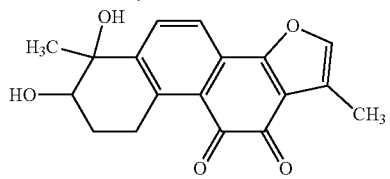

Tanshinondiol B

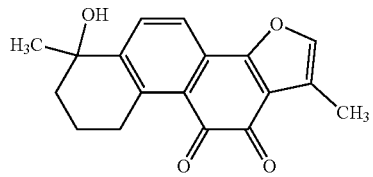

3-hydroxytanshinone IIA

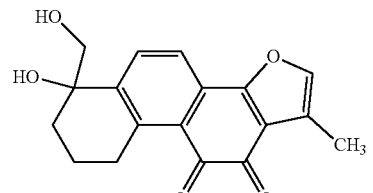

Tanshinondiol A

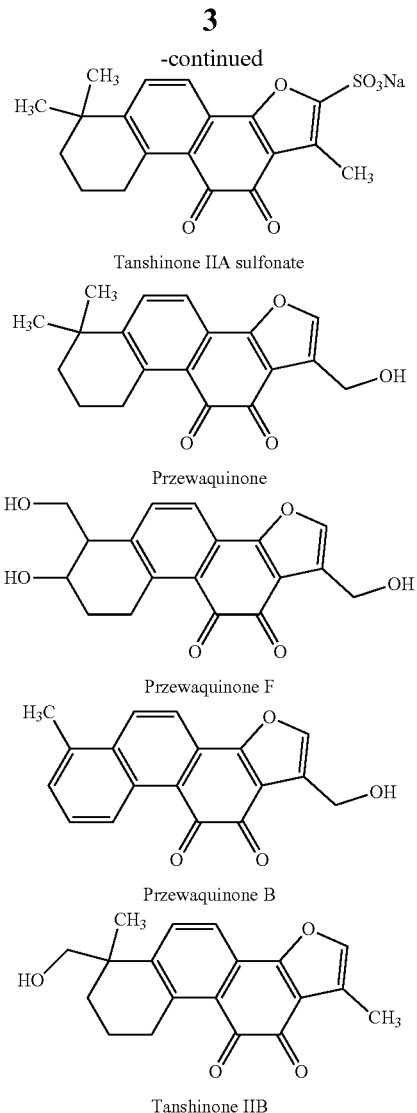

Tanshinone IIA sulfonate

Przewaquinone

Przewaquinone F

Przewaquinone B

Tanshinone IIB

Tanshinone I has poor solubility in water, and thus has low in vivo bioavailability. Therefore, scientists have attempted to modify the structure of tanshinone I in order to improve its water solubility and bioavailability so as to magnify the medicinal value of tanshinone I. (QIN Yinlin, Tanshinone I derivatives and applications thereof in pharmaceuticals, [P] CN 1837199A, 2006; QIN Yinlin, Tanshinone I derivatives and applications thereof in pharmaceuticals, [P] CN 1837200A, 2006; DU Zhiyun et al., Tanshinone derivatives and applications thereof in the preparation of a medicament for aldose reductase inhibitors, [P] CN 101012270A, 2007.)

Tanshinone I possesses certain antitumor effects. It is reported that, by observing the effects of tanshinone I on various indices of Hep G2 cells in in vitro and in vivo experiments, one can make an overall judgment whether it possesses anti-tumor effects. Results from the in vitro experiments indicate that tanshinone I can inhibit the proliferation of Hep G2 cells. In addition, results from the tumor inhibition experiments carried out on tumor-bearing nude mice indicate that tanshinone I can inhibit the tumor growth in the mice. That is, tanshinone I possesses antitumor effects in vivo as well. (ZHENG Guocan, L I Zhiying, Study on the inhibiting effect of Tanshinone I on HepG2 cell line in vitro, Modern Medical Journal, 2004, 32 (15): 296-298; ZHENG Guocan, L I Zhiying, Study on the anti-tumor effect and mechanism of tanshinone I, Journal of Practical Oncology, 2005, 20 (1): 33-35).

In addition, some studies have reported the effects of tanshinone I on the proliferation and apoptosis of SGC-7901 gastric adenocarcinoma cells in vitro. Experiments have found out that tanshinone I has significant inhibitory effect on the growth of the SGC-7901 human gastric adenocarcinoma cells cultured in vitro, and the inhibition of the cell growth is dependent on the concentration of tanshinone I within a certain range. (ZHOU Xiaoli et al., The effect of Tanshinone I on proliferation and apoptosis of human gastric adenocarcinoma cell line SGC-7901, Journal of Modern Oncology, 2011, 19 (3): 423-427.)

In spite of the multitude of studies on the structural modifications and bioactivity of tanshinone I, reports on the synthesis and application of antitumor tanshinone compounds with good water solubility, low toxicity and excellent bioactivity have not yet been seen.

SUMMARY OF THE INVENTION

One object of the present invention is to provide 2-alkyl- or 2-aromatic-substituted tanshinone I derivatives of formula (I),

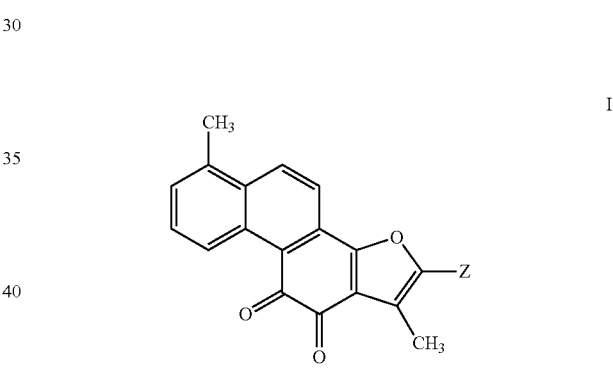

I which when Z=R, represents 2-alkyl-substituted tanshinone I of formula I-1;

when Z=Ar, represents 2-aryl-substituted tanshinone I of formula I-2; and when Z=Het, represents 2-heteroaryl- or 2-heterocyclyl-substituted tanshinone I of formula I-3,

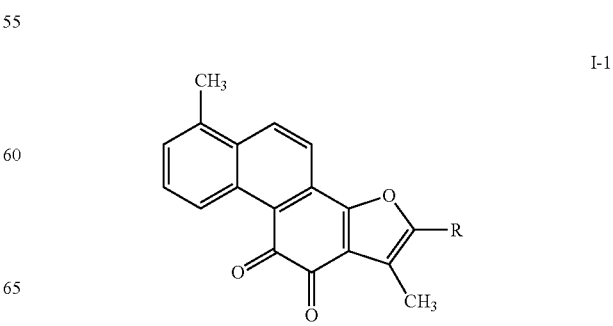

I-1

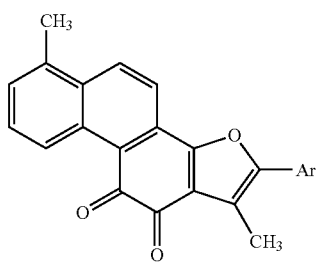

I-2

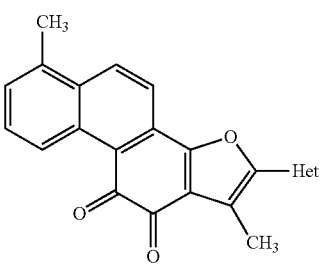

I-3 wherein

R is selected from substituted or unsubstituted $C_1$-$C_{18}$ alkyl, substituted or unsubstituted $C_2$-$C_{18}$ alkenyl or alkynyl, and substituted or unsubstituted $C_3$-$C_7$ cycloalkyl or cycloalkenyl;

Ar is selected from substituted or unsubstituted aryl;

Het is selected from substituted or unsubstituted heteroaryl or heterocyclyl;

each of the aforementioned substituted group is substituted by one or more substituents selected from the group consisting of halogen, amino, $C_1$-$C_6$ substituted amino, nitro, cyano, $C_1$-$C_6$ alkoxy, thiol, $C_1$-$C_6$ alkylthio, and a water soluble functional group; and Ar may further be substituted with $C_1$-$C_6$ alkyl; or a pharmaceutically acceptable salt thereof.

The second object of the present invention is to provide a process for preparing the 2-alkyl- or 2-aromatic-substituted tanshinone I derivatives of formula (I) of the present invention:

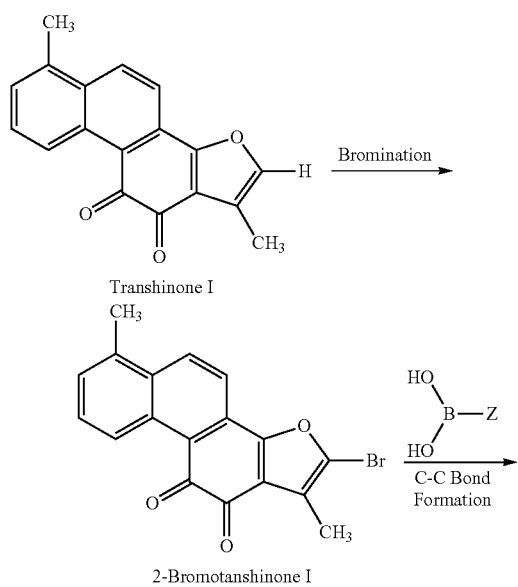

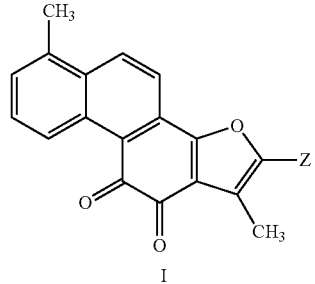

I

The 2-alkyl- or 2-aromatic-substituted tanshinone I derivatives of formula (I) of the present invention can be prepared in a two-step reaction as shown above, comprising firstly reacting tanshinone I (TA) with a brominating agent to produce a 2-bromotanshinone I intermediate; then subjecting the 2-bromotanshinone I intermediate to C—C bond formation with corresponding organic boric acid or borate in the presence of a catalyst to produce a 2-alkyl- or 2-aromatic-substituted tanshinone I derivative of formula (I), wherein Z is as defined above for formula (I); and optionally further subjecting the resulted compound to derivatization to produce other compounds of formula (I).

The third object of the present invention is to provide a pharmaceutical composition comprising the compound of the present invention, said pharmaceutical composition comprising at least one compound of the present invention and optionally a pharmaceutically acceptable excipient.

The fourth object of the present invention is to provide the use of the compound of the present invention or the pharmaceutical composition comprising the compound in the manufacture of a medicament, in particular an antitumor medicament. Correspondingly, the present invention provides a method for treating a subject suffering from tumor, comprising administrating to the subject in need thereof an effective amount of at least one compound of the present invention. Said tumor is particularly selected from leukemia, multiple myeloma, lymphoma, liver cancer, gastric cancer, breast cancer, cholangiocellular carcinoma, pancreatic cancer, lung cancer, colorectal cancer, osteosarcoma, melanoma, human cervical cancer, glioma, nasopharyngeal carcinoma, laryngeal carcinoma, esophageal cancer, middle ear tumor, prostate cancer, and the like.

The present invention also relates to the compounds of the present invention used for treating a tumor.

The fifth object of the present invention is to provide the following intermediate compounds,

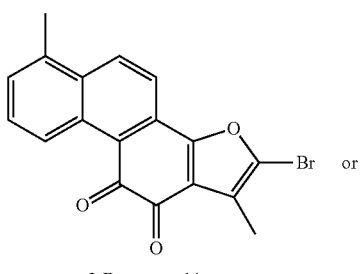 or

2-Bromotanshinone

-continued

BS-TA-31

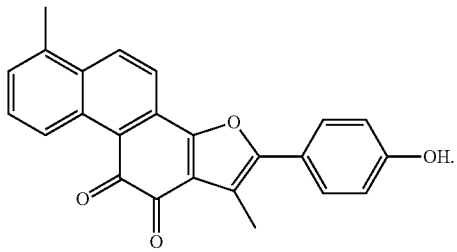

SPECIFIC EMBODIMENTS OF THE INVENTION

The present invention relates to a novel 2-alkyl- or 2-aromatics-substituted tanshinone I derivative of formula (I),

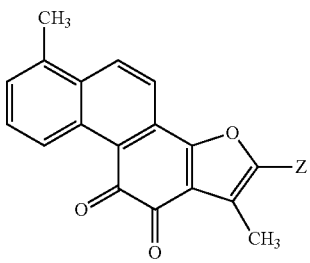

which when Z=R, represents 2-alkyl-substituted tanshinone I of formula I-1;

when Z=Ar, represents 2-aryl-substituted tanshinone I of formula I-2; and when Z=Het, represents 2-heteroaryl- or 2-heterocyclyl-substituted tanshinone I of formula I-3,

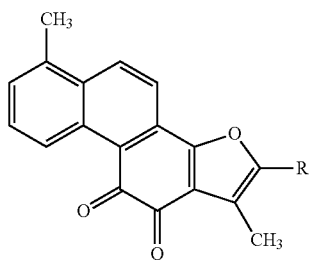

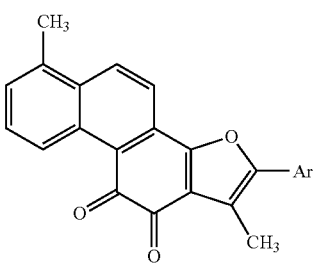

-continued

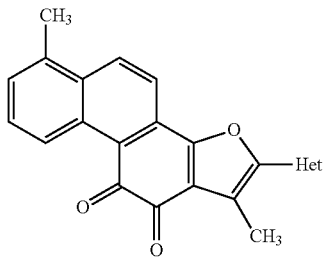

wherein R is selected from substituted or unsubstituted $C_1$-$C_{18}$ alkyl, substituted or unsubstituted $C_2$-$C_{18}$ alkenyl or alkynyl, substituted or unsubstituted $C_3$-$C_7$ cycloalkyl or cycloalkenyl;

Ar is selected from substituted or unsubstituted aryl;

Het is selected from substituted or unsubstituted heteroaryl or heterocyclic radical;

each of the aforementioned substituted group is substituted by one or more substituents selected from the group consisting of halogen, amino, $C_1$-$C_6$ substituted amino, nitro, cyano, $C_1$-$C_6$ alkoxy, thiol, $C_1$-$C_6$ alkylthio, and a water soluble functional group; and Ar may further be substituted with $C_1$-$C_6$ alkyl;

or a pharmaceutically acceptable salt thereof.

The compound of formula (I) of the present invention possesses antitumor activity.

According to a preferred embodiment of the present invention, R is not a carboxyl-substituted $C_1$-$C_{18}$ alkyl or a carboxyl-substituted $C_2$-$C_{18}$ alkenyl, and R is not a methyl substituted with an amino or with a substituted amino.

According to another preferred embodiment of the present invention, the water soluble functional group is selected from hydroxyl, polyhydroxy alkoxy, saccharide residue, carboxyl, sulfonic acid group, phosphate group, polyhydroxy alkoxy carbonyl, carboxyl alkoxy, and carboxyl alkyl formyloxy; wherein the alkoxy and alkyl in the aforementioned groups have 1-8 carbon atoms, respectively.

According to a preferred embodiment of the present invention, Z represents aryl or heteroaryl. According to a particularly preferred embodiment of the present invention, Z represents phenyl.

According to another preferred embodiment of the present invention, R is $C_1$-$C_{12}$ alkyl, preferably $C_1$-$C_6$ alkyl, and more preferably methyl.

According to a preferred embodiment of the present invention, Ar is halogen-substituted phenyl and preferably chlorine-substituted phenyl.

According to another preferred embodiment of the present invention, Ar is $C_1$-$C_6$ alkoxy-substituted phenyl and preferably methoxy-substituted phenyl.

According to a particularly preferred embodiment of the present invention, as compared with extracted and separated natural tanshinone I (TA), the compound of formula (I) of the present invention contains more water soluble groups and in the meantime has improved antitumor activity, and those particularly preferred compounds even improve their antitumor activity by several folds. For example, such compounds are the compounds of formula (I) wherein Ar is polyhydroxy-alkoxy-substituted phenyl, said polyhydroxy alkoxy being preferably of 3-7 carbon atoms and more preferably being glycerin residue; or Ar is saccharide-residue-substituted phenyl, preferably a phenyl substituted by glucose-residue. Further as an example, the compounds of formula (I) has a phenyl substituted by carboxyl, sulfo, or phosphate group as the Ar group.

In an embodiment, the present invention relates to the compounds of formula (I), wherein R, Ar and Het are selected from corresponding boric acid or borate.

Some preferred 2-alkyl- or 2-aromatic-substituted tanshinone I derivatives according to the present invention is shown as below. These examples are only intended to further illustrate the present invention but not to make any restriction of the scope of the present invention.

-continued

BS-TA-09

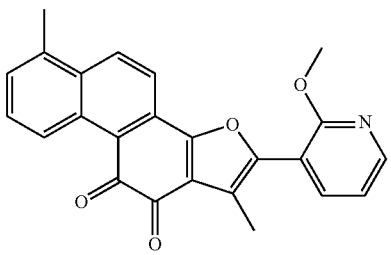

BS-TA-01

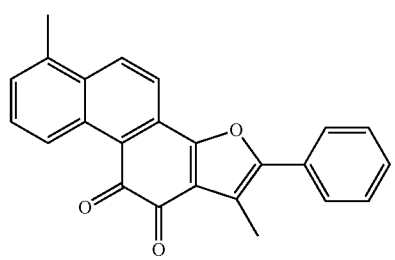

BS-TA-14

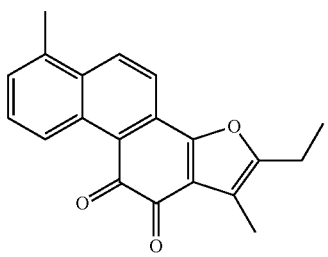

BS-TA-03

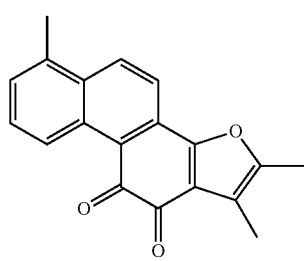

BS-TA-41

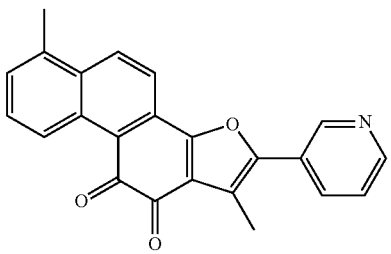

BS-TA-04

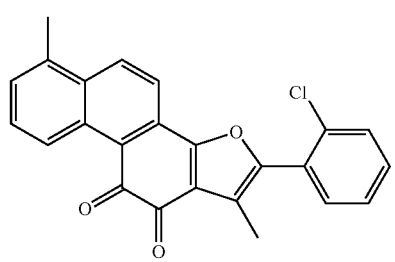

BS-TA-31

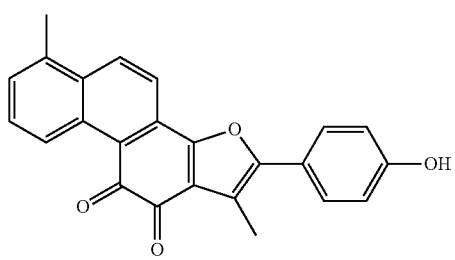

BS-TA-06

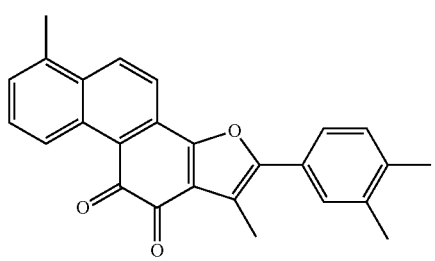

BS-TA-32

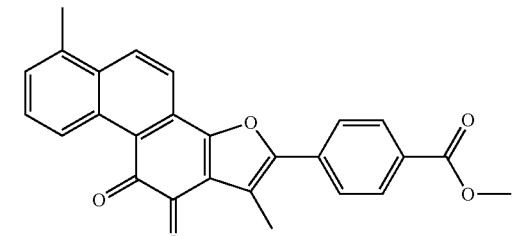

BS-TA-07

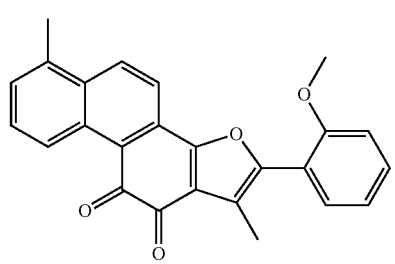

BS-TA-301

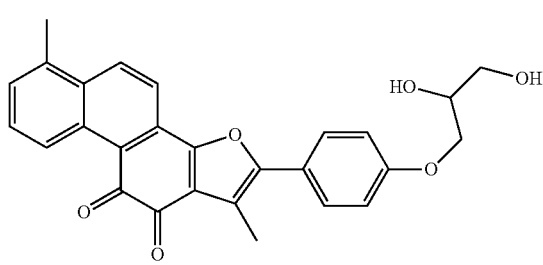

-continued

BS-TA-302
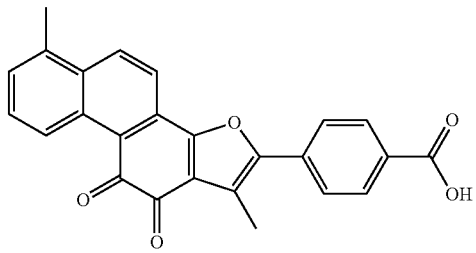

BS-TA-306
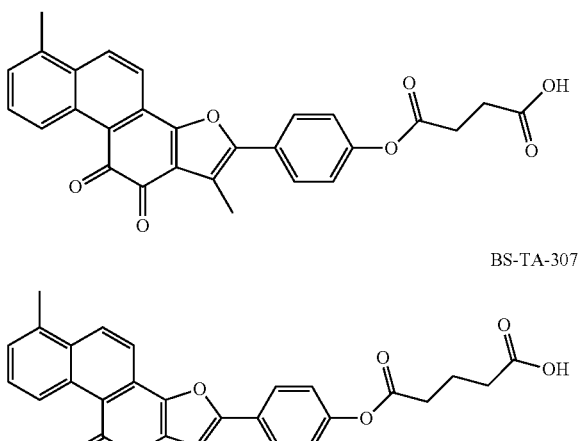

BS-TA-307
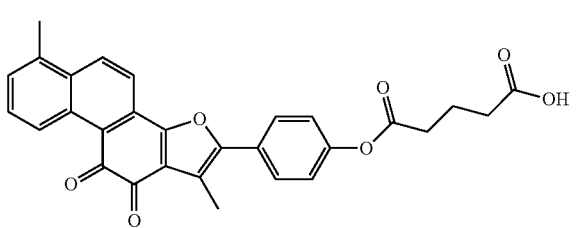

BS-TA-309
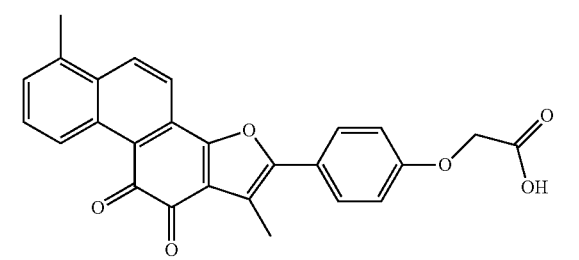

Some data for the above compounds are listed in the table below:

| Compound No. | Formula | Molecular Weight | Appearance | State | Total Yield (%) |
|---|---|---|---|---|---|
| BS-TA-01 | $C_{24}H_{16}O_3$ | 352.39 | Black | Solid | 3 |
| BS-TA-03 | $C_{19}H_{14}O_3$ | 290.32 | Black | Solid | 21 |
| BS-TA-04 | $C_{24}H_{15}ClO_3$ | 386.84 | Brown | Solid | 20 |
| BS-TA-06 | $C_{26}H_{20}O_3$ | 380.45 | Black | Solid | 1 |
| BS-TA-07 | $C_{25}H_{18}O_4$ | 382.42 | Brown | Solid | 5 |
| BS-TA-09 | $C_{24}H_{17}NO_4$ | 383.41 | Black | Solid | 2 |
| BS-TA-14 | $C_{20}H_{16}O_3$ | 304.35 | Brown | Solid | 2 |
| BS-TA-41 | $C_{23}H_{15}NO_3$ | 353.38 | Brown | Solid | 29 |
| BS-TA-31 | $C_{24}H_{16}O_4$ | 368.39 | Brown | Solid | 58 |
| BS-TA-32 | $C_{26}H_{18}O_5$ | 410.43 | Brown | Solid | 53 |
| BS-TA-301 | $C_{27}H_{22}O_6$ | 442.47 | Brown | Solid | 34 |
| BS-TA-302 | $C_{25}H_{16}O_5$ | 396.40 | Brown | Solid | 19 |
| BS-TA-306 | $C_{28}H_{20}O_7$ | 468.47 | Brown | Solid | 28 |
| BS-TA-307 | $C_{29}H_{22}O_7$ | 482.49 | Red | Solid | 16 |
| BS-TA-309 | $C_{26}H_{18}O_6$ | 426.43 | Brown | Solid | 22 |

In another embodiment, the present invention particularly prefers the following compounds of formula (I):

BS-TA-03
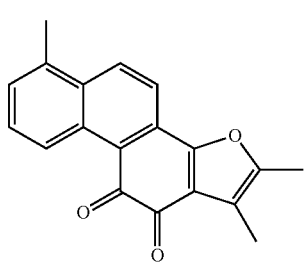

2-methyl-tanshinone I

BS-TA-04
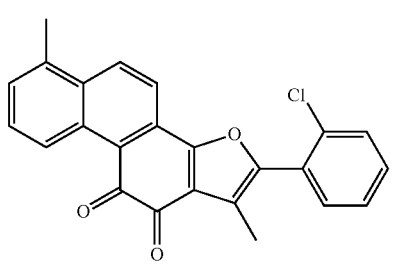

2-o-chlorophenyl-tanshinone I

BS-TA-07
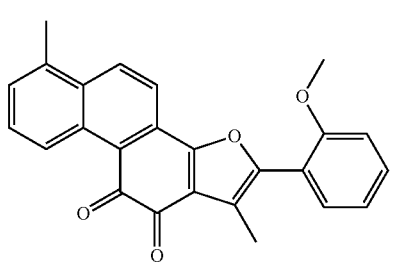

2-o-methoxyphenyl-tanshinone I

BS-TA-14
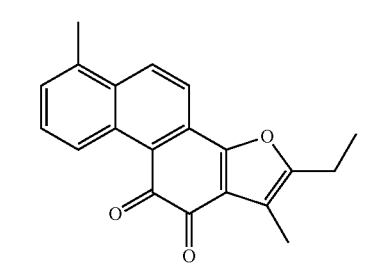

2-ethyl-tanshinone I

BS-TA-301
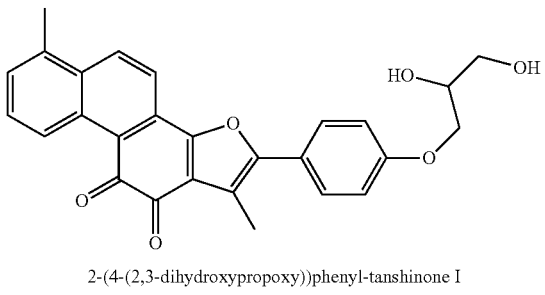

2-(4-(2,3-dihydroxypropoxy))phenyl-tanshinone I

-continued

BS-TA-302

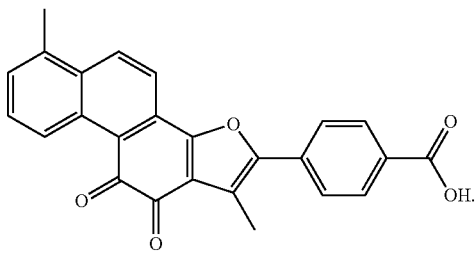

p-carboxylphenyl-tanshinone I

As used herein, the term "alkyl" refers to a straight or branched hydrocarbon radical containing designated number of carbon atoms, such as $C_1$-$C_{18}$ alkyl, $C_1$-$C_{12}$ alkyl, $C_1$-$C_6$ alkyl, $C_1$-$C_5$ alkyl, $C_1$-$C_4$ alkyl, $C_1$-$C_3$ alkyl, etc. Examples of alkyl include, but not limited to, methyl, ethyl, n-propyl, isopropyl, tert-butyl, n-pentyl, n-hexyl and n-octadecyl.

The term "alkenyl" refers to a straight or branched alkenyl containing designated number of carbon atoms, such as $C_2$-$C_{18}$ alkenyl, $C_2$-$C_{12}$ alkenyl, $C_2$-$C_6$ alkenyl, $C_2$-$C_5$ alkenyl, $C_2$-$C_4$ alkenyl, $C_2$-$C_3$ alkenyl, etc. Examples of $C_2$-$C_{18}$ alkenyl include, but not limited to, vinyl, allyl and octadecenyl.

The term "$C_3$-$C_7$ cycloalkyl or cycloalkenyl" refers to a saturated or unsaturated 3-7 membered monocyclic hydrocarbon radical. $C_3$-$C_7$ cycloalkyl or cycloalkenyl can be cyclopropyl, cyclobutyl, cyclopentyl, cyclohexyl, cycloheptyl, cyclopropenyl and cyclohexenyl.

The term "aryl" refers to a monocyclic aryl or polycyclic aryl, fused or unfused, containing 6-14 (such as 6-12, 6-10) carbon atoms. In the case of polycyclic aryl, at least one ring is aromatic. Aryl can also be one fused with a heterocycyl radical. Examples of aryl include phenyl, biphenyl, naphthyl, 5,6,7,8-tetrahydronaphthyl, 2,3-dihydrobenzofuranyl, etc.

The term "heteroaryl" refers to an aromatic ring group having 1-4 heteroatoms (e.g. 1, 2, 3 or 4 heteroatoms) in the ring as ring atom(s). A heteroatom refers to nitrogen, oxygen or sulfur. A heteroaryl can be a monocyclic heteroaryl having 5-7 ring atoms or a bicyclic heteroaryl having 7-11 ring atoms. Said bicyclic heteroaryl should comprise at least one aromatic heterocycle, and the other can be aromatic or non-aromatic, with or without a heteroatom. Examples of heteroaryl include such as pyrrolyl, pyrazolyl, imidazolyl, oxazolyl, pyridyl, pyrimidinyl, furanyl, thienyl, isoxazolyl, indolyl, etc.

The term "heterocyclyl" refers to a non-aromatic cyclic group containing 1-4 heteroatoms (e.g. 1, 2, 3 or 4 heteroatoms) as ring members. A heteroatom refers to nitrogen, oxygen or sulfur. A heterocyclyl can be a monocyclic heterocyclyl having 4-8 ring atoms (such as 4-7 membered ring, 5-7 membered ring, and 5-6 membered ring) or a bicyclic heterocyclyl having 7-11 ring atoms. Examples of heterocyclyl include azetidinyl, pyrrolidinyl, pyrrolinyl, tetrahydrofuranyl, dihydrofuranyl, piperazinyl, piperidinyl, morpholinyl, thiomorpholinyl, tetrahydropyranyl, tetrahydrothienyl, etc.

The term "halogen" refers to fluorine, chlorine, bromine or iodine.

The term "alkyl-substituted amino" refers to —N-alkyl.
The term "alkoxy" refers to —O-alkyl.
The term "alkylthio" refers to —S-alkyl.

The term "polyhydroxy alkoxy" refers to alkoxy substituted with two or more hydroxyls, preferably an alkoxy comprising 3-7 carbon atoms, and preferably being dihydroxy propoxy, trihydroxy butoxy, tetrahydroxy pentoxy, etc.

The term "saccharide residue" refers to saccharide residue after removing one hydrogen atom from saccharide hydroxyl. Said saccharide is preferably monosaccharide comprising 3-7 carbon atoms, such as triose, tetrose, pentose, hexose or heptose.

As used herein, the term "pharmaceutically acceptable salts of the compounds of formula (I)" can be exemplified by the organic acid salts formed by an organic acid which comprises a pharmaceutically acceptable anion. These organic acid salts include, but not limited to, tosylate, methanesulfonate, malate, acetate, citrate, malonate, tartrate, succinate, benzoate, ascorbate, lactate, α-ketoglutarate, and α-glycerophosphate. Suitable inorganic salts may also be formed, including but not limited to, hydrochloride, sulfate, nitrate, bicarbonate and carbonate, phosphate, hydrobromate, hydriodate and the like.

A pharmaceutically acceptable salt may be obtained using standard procedures well known in the art, for example by reacting a sufficient amount of alkaline compound with a suitable acid that provides a pharmaceutically acceptable anion.

The terms "treatment," "treating," "treat," and the like used herein refer generally to obtaining a desired pharmacological and/or physiological effect. The effect may be prophylactic in terms of completely or partially preventing a disease or symptoms thereof and/or may be therapeutic in terms of partial or complete stabilization or cure of a disease and/or adverse effects caused by the disease. "Treatment" as used herein covers any treatment of a disease in a subject, including: (a) preventing the disease or symptoms from occurring in a subject who is predisposed to the disease or symptoms but has not yet been diagnosed as having it; (b) inhibiting the symptoms of a disease, i.e., arresting its development; or (c) relieving the symptoms of a disease, i.e., causing regression of the disease or symptoms.

The compounds of the present invention can be prepared through a conventional organic chemistry synthesis process. For example, the compound of formula (I) of the present invention can be prepared as follows.

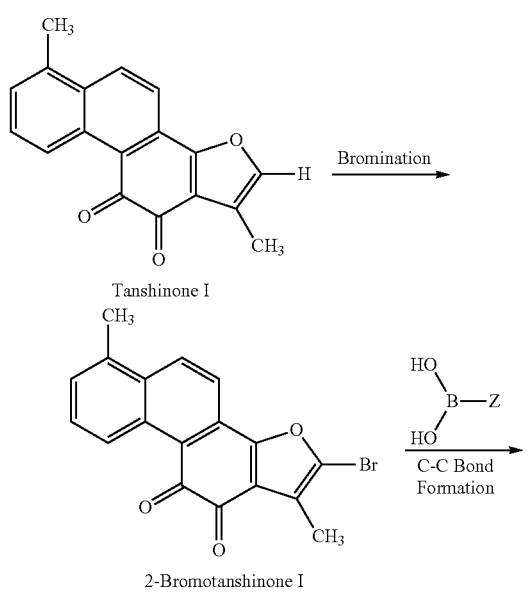

Tanshinone I

2-Bromotanshinone I

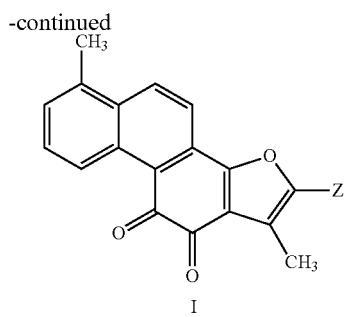

I

The 2-alkyl- or 2-aromatic-substituted tanshinone I derivative of formula (I) can be prepared as follows: firstly subjecting naturally extracted and separated tanshinone I (TA) to bromination to produce a 2-bromotanshinone I intermediate; subjecting said intermediate to a C—C bond formation reaction with corresponding organic boric acid or borate in the presence of a catalyst to produce a 2-alkyl- or 2-aromatic-substituted tanshinone I derivative of formula (I), wherein Z is as defined above for formula (I); and optionally further subjecting the resulted compound to derivatization to produce other compounds of formula (I).

The above bromination is typically carried out in the presence of an active brominating agent. The brominating agent here can be, but not limited to, N-bromosuccinimide and bromine water.

The above bromination is typically carried out in a solvent. The solvent used can be, but not limited to, polar solvents, such as N,N-dimethylformamide, etc.

The above bromination is typically carried out at a temperature of from 0° C. to 40° C. The reaction can typically be carried out at room temperature.

The material for the bromination is tanshinone I (TA). This material is obtained by extracting and separating natural medicines and is commercially available. The organic boric acid and borate used for the C—C bond formation are all commercially available.

The 2-bromotanshinone I intermediate is then subjected to C—C bond formation with corresponding organic boric acid or borate in the presence of a catalyst to produce a 2-alkyl- or 2-aromatic-substituted tanshinone I derivative of formula (I).

The C—C bond formation is typically carried out in the presence of a palladium catalyst. The palladium catalyst used here can be, but not limited to, tetra(triphenylphosphine)palladium (Pd(PPh$_3$)$_4$), palladium acetate (Pd(OAc)$_2$), and [1,1'-bis(diphenylphosphino)ferrocene] palladium dichloride (Pd(dppf)Cl$_2$).

The organic boronic reagent used for the C—C bond formation typically requires the protection, by using a protecting group, of functional groups other than boric acid or borate. The protecting group used will finally be removed.

The C—C bond formation is typically carried out in the presence of an alkali. The alkali herein can be either organic alkalis or inorganic alkalis, such as potassium phosphate, sodium carbonate, sodium ethoxide, triethylamine, etc.

The C—C bond formation is typically carried out in a solvent. The solvent used comprises, but not limited to, organic polar solvents, such as dichloromethane (DCM), tetrahydrofuran (THF), N,N-dimethylformamide (DMF), dimethylsulfoxide (DMSO), etc.

The C—C bond formation is typically carried out under heating. The reaction temperature depends on the activity of the boronic reagent and is typically from 50° C. to 60° C.

The preparation of the 2-alkyl- or 2-aromatic-substituted tanshinone I derivative of formula (I) is typically operated according to the following general process. Tanshinone I and N-bromosuccinimide are reacted at room temperature in N,N-dimethylformamide (DMF) to produce a 2-bromotanshinone I. The general operation of the C—C bond formation can be, but not limited to, the following: to the solvent N,N-dimethylformamide (DMF) are added 2-bromotanshinone I, a palladium catalyst and an alkali in a suitable proportion, and a catalytic amount of ligand may also be added. The reaction is heated and stirred for 24 hours, and the resulted product is extracted with an organic solvent, washed with water and saturated brine, dried and concentrated to give the crude product. The crude product is then purified with a silica-gel column or via HPLC to give the pure product.

Conventional chemical conversion processes may be used to practice this invention. One skilled person in the art can determine suitable chemical agents, solvents, protecting groups, and reaction conditions for these chemical conversions. Relevant information are described, for example, in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Protecting groups refer to the groups that, upon being attached to an active moiety (e.g., a hydroxyl or amino group), prevent the moiety from being influenced in a subsequent reaction and, after the reaction, can be removed through a conventional method. Examples of a hydroxyl protecting group include, but not limited to, alkyl, benzyl, allyl, trityl (also known as triphenylmethyl), acyl (e.g., benzoyl, acetyl, or HOOC—X"—CO—, wherein X" is alkylidene, alkenylene, cycloalkylene, or arylene), silyl (e.g., trimethylsilyl, triethylsilyl, and t-butyldimethylsilyl), alkoxylcarbonyl, aminocarbonyl (e.g., dimethylaminocarbonyl, methylethylaminocarbonyl, and phenylaminocarbonyl), alkoxymethyl, benzyloxymethyl, and alkylmercaptomethyl. Examples of an amino protecting group include, but not limited to, alkoxycarbonyl, alkanoyl, aryloxycarbonyl, aryl-substituted alkyl and the like. Hydroxyl and amino protecting groups have been discussed in T. W. Greene and P. G. M. Wuts, Protective Groups in Organic Synthesis, 2nd. Ed., John Wiley and Sons (1991). All hydroxyl and amino protecting groups can be removed by a conventional method after the reaction.

Specifically, among the preferred compounds of formula (I) of the present invention, BS-TA-03, BS-TA-01, BS-TA-04, BS-TA-06, BS-TA-07, BS-TA-09, BS-TA-14, BS-TA-41, BS-TA-31 and BS-TA-32 are prepared with naturally extracted and separated tanshinone I (TA) as the starting material through the above two-step reaction.

BS-TA-301 is obtained by etherification and ring-opening of BS-TA-31 as the starting material.

BS-TA-302 is obtained by hydrolysis of BS-TA-32 as the starting material.

BS-TA-306 and BS-TA-307 are obtained by esterification of BS-TA-31 as the starting material.

BS-TA-301 is obtained by etherification and hydrolysis of BS-TA-31 as the starting material.

The present invention also provides a pharmaceutical composition comprising the compound of formula (I) of the present invention.

The present invention provides a pharmaceutical composition which comprises at least one compound of formula (I) of the present invention as defined above and optionally a pharmaceutically acceptable excipient.

The methods for preparing various pharmaceutical compositions having a given amount of active components are known or would be apparent to those skilled in the art in light of this disclosure. For example, description can be found in REMINGTON'S PHARMACEUTICAL SCIENCES, Martin, E. W., ed., Mack Publishing Company, 19th ed. (1995). Methods for preparing such pharmaceutical compositions include incorporation of other suitable pharmaceutical excipients, carriers, diluents, etc.

The pharmaceutical preparations of the present invention are produced by known methods, including conventional mixing, dissolving, or freeze drying processes.

The compounds of the present invention may be formulated into a pharmaceutical composition and administered to any subject in a route suitable for the selected administration manner, e.g., orally or parenterally (for example, by an intravenous, intramuscular, topical or subcutaneous route).

Thus, the present compounds may be systemically administered, e.g., orally administered, in combination with a pharmaceutically acceptable carrier such as an inert diluent or an assimilable, edible carrier. They may be enclosed in hard or soft gelatin capsules, or may be compressed into tablets. For therapeutic oral administration, the active compound may be combined with one or more excipients and may be taken in a form of ingestible tablet, buccal tablet, troche, capsule, elixir, suspension, syrup, wafer, and the like. Such a composition or preparation should contain at least 0.1% of the active compound. Of course, the proportion of active compound in the compositions and preparations may vary and may be from about 1% to about 99% by weight of a given unit dosage form. In a therapeutically useful composition, the active compound is present in an amount such that an effective dosage level is achieved.

A tablet, troche, pill, capsule and the like may also comprise a binder, such as gum tragacanth, arabic gum, corn starch or gelatin; an excipient such as calcium dihydrogenphosphate; a disintegrating agent such as corn starch, potato starch, alginic acid and the like; a lubricant such as magnesium stearate; and a sweetening agent such as sucrose, fructose, lactose or aspartame; or a flavoring agent such as peppermint, wintergreen oil, or cherry flavor. In case the unit dosage form is a capsule, it may comprise, in addition to the above materials, a liquid vehicle such as a vegetable oil or polyethylene glycol. Various other materials may be present as coatings or otherwise modify the physical form of the solid unit dosage form. For instance, a tablet, pill, or capsule may be coated with gelatin, wax, shellac or sugar, etc. A syrup or elixir may contain an active compound, a sweetening agent such as sucrose or fructose, a preservative such as methylparaben or propylparaben, a dye and a flavoring agent (such as cherry or orange flavor). Of course, any materials used in preparing unit dosage forms should be pharmaceutically acceptable and substantially non-toxic in the amounts employed. In addition, the active compound may be incorporated into a sustained-release preparation or device.

The active compound may also be administered intravenously or intraperitoneally by infusion or injection. An aqueous solution of the active compound or its salt may be prepared, optionally mixed with a nontoxic surfactant. Also can be prepared is dispersion in glycerol, liquid polyethylene glycol, triacetin, or a mixture thereof, or in an oil. Under ordinary storage and use conditions, these preparations contain a preservative to prevent the growth of microorganisms.

The pharmaceutical dosage forms suitable for injection or infusion may include a sterile aqueous solution, a dispersion or a sterile powder comprising active ingredients (optionally encapsulated in liposomes), which are adapted for an extemporaneous preparation of a sterile injectable or infusible solution or dispersion. In all cases, the final dosage form must be sterile and stable liquids under the manufacture and storage conditions. The liquid carrier or vehicle may be a solvent or a liquid dispersion medium comprising, for example, water, ethanol, a polyol (for example, glycerol, propylene glycol, liquid polyethylene glycol, and the like), a vegetable oil, a nontoxic glyceride, and a suitable mixture thereof. A proper fluidity can be maintained, for example, by formation of liposomes, by maintenance of the required particle size in the case of dispersion or by the use of a surfactant. The prevention of microorganism can be achieved by various antibacterial and antifungal agents, such as parabens, chlorobutanol, phenol, sorbic acid, thimerosal, and the like. In many cases, an isotonic agent is preferably comprised, such as sugar, buffer agent or sodium chloride. Prolonged absorption of an injectable composition can be obtained by the use of a composition of the agents for delaying absorption, for example, aluminum monostearate and gelatin.

An injectable sterile solution is prepared by combining a required amount of the active compound in a suitable solvent with various additional desired components as listed above, followed by filtration and sterilization. For sterile powder used to prepare an injectable sterile solution, the preferred preparation process is vacuum drying and freeze drying techniques, which yield a powder of the active ingredient plus any additional desired ingredient present in the previous filtered sterile solution.

Useful solid carriers include finely divided solids such as talc, clay, microcrystalline cellulose, silica, alumina and the like. Useful liquid carriers include water, ethanol or ethylene glycol or a water-ethanol/ethylene glycol mixture, in which the compound of the present invention can be dissolved or dispersed at an effective content, optionally with the aid of a non-toxic surfactant. An adjuvant (such as a flavour) and additional antimicrobial agent can be added to optimize the properties for a given application.

Thickening agent (such as a synthetic polymer, a fatty acid, a fatty acid salt and ester, a fatty alcohol, a modified cellulose or a modified inorganic material) can also be used with a liquid carrier to form a spreadable paste, gel, ointment, soap and the like for applying directly to the skin of a user.

The amount of the compound or an active salt or derivative thereof required for a treatment varies depending not only on the selected particular salt but also on the administration route, the nature of the condition to be treated and the age and condition of the subject, and will be ultimately determined at the discretion of the attendant physician or clinician.

The above formulations can be present in a unit dosage form which is a physically discrete unit containing a unit dosage, which is suitable for administering to a human or other mammalians. The unit dosage form may be a capsule or a tablet, or a plurality of capsules or tablets. Depending upon the intended particular therapy, the amount of the active ingredient in a unit dosage form can be varied or adjusted in the range of about 0.1 mg to about 1,000 mg or more.

The present invention also provides the use of a compound according to the present invention or a pharmaceutical composition comprising the compound of the present invention in manufacture of a medicament, especially an antitumor medicament. Accordingly, the present invention provides a method for treating a subject suffering from tumor, comprising administering to the subject in need thereof a therapeutically effective amount of at least one compound of the present invention. The 2-alkyl- or 2-aromatic-substituted tanshinone I derivative of the present invention or a pharmaceutically acceptable salt thereof can be used, for example, for the treatment of leukemia, multiple myeloma, lymphoma, liver cancer, gastric cancer, breast cancer, cholangiocellular carcinoma, pancreatic cancer, lung cancer, colorectal cancer, osteosarcoma, melanoma, cervical cancer, glioma, nasopharyngeal carcinoma, laryngeal carcinoma, esophageal cancer, middle ear tumor, prostate cancer, etc.

The present invention will be explained in more detailed by the following examples. However, it should be understood that the following examples are intended for illustration only but not to limit the scope of the present invention in any way.

The raw chemicals used in the following examples are commercially available or may be prepared by a synthesis method known in the art.

EXAMPLE 1

Synthesis of Compound BS-TA-03

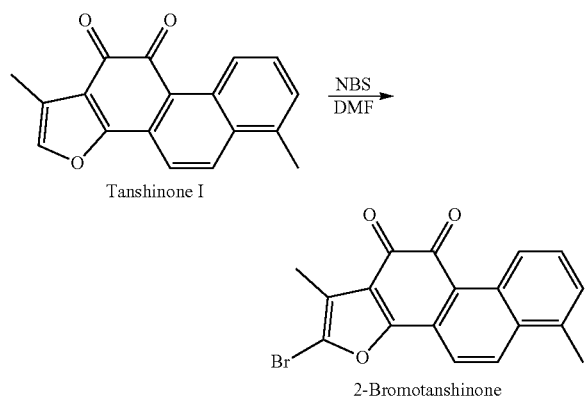

Tanshinone I

2-Bromotanshinone wherein, DMF is N,N-dimethylformamide, and NBS is N-bromosuccinimide.

To N,N-dimethylformamide (30 mL) are added tanshinone I (1 g, 3.6 mmol) and N-bromosuccinimide (0.67 g, 3.78 mmol). After stirring for 3 hours at room temperature, the resulted precipitates are filtered. Residue is washed with water and saturated solution of sodium bicarbonate and dried to give 2-bromotanshinone I (0.82 g, yield 63.8%).

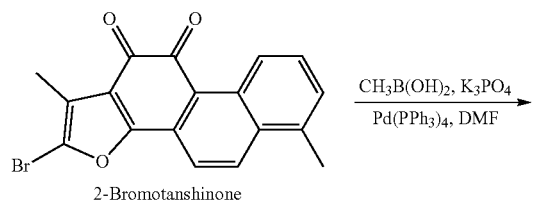

2-Bromotanshinone

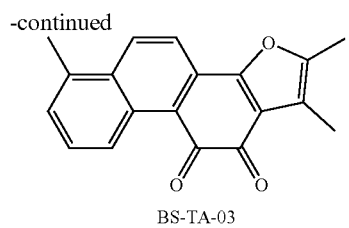

BS-TA-03 wherein, $CH_3B(OH)_2$ represents methylboric acid, $K_3PO_4$ represents potassium phosphate, and $Pd(PPh_3)$ represents tetra(triphenylphosphine)palladium.

Under nitrogen protection, to N,N-dimethylformamide (10 mL) are added 2-bromotanshinone I (100 mg, 0.28 mmol), methylboric acid (20 mg, 0.34 mmol) and potassium phosphate (148 mg, 0.7 mmol), and then tetra(triphenylphosphine)palladium (388 mg, 0.34 mmol) is added. After the reaction solution is heated up to 100° C. and stirred for 16 hours, water is added thereto. Dichloromethane is used for extraction. The organic phase is washed with saturated solution of sodium bicarbonate and dried with anhydrous sodium sulfate. The crude product resulted from concentration is separated and purified via preparative chromatography to give the compound BS-TA-03 (5.9 mg, yield 8%) as a black solid.

LC-MS: retention time: 3.10 min (98.6%); m/z: 291.1 (M+H).

$^1$H NMR (300 MHz, CDCl$_3$) δ 9.220 (d, 1H), 8.246 (d, 1H), 7.749 (d, 1H), 7.528 (m, 1H), 7.337 (m, 1H), 2.680 (s, 3H), 2.332 (s, 3H), 2.191 (s, 3H).

BS-TA-01 is prepared according to the process for BS-TA-03 using the same reagents as above by reacting the compound 2-bromotanshinone I with phenylboric acid.

LC-MS: retention time: 3.40 min (99.07%), m/z: 353.0 (M+H).

BS-TA-04 is prepared according to the process for BS-TA-03 using the same reagents as above by reacting the compound 2-bromotanshinone I with 2-chlorophenylboric acid.

LC-MS: retention time: 3.44 min (99.62%), m/z: 387.0 (M+H).

$^1$H NMR (300 MHz, CDCl$_3$) δ 9.271 (d, 1H), 8.333 (d, 1H), 7.895 (d, 1H), 7.575 (m, 3H), 7.444 (m, 3H), 2.702 (s, 3H), 2.318 (s, 3H).

BS-TA-06 is prepared according to the process for BS-TA-03 using the same reagents as above by reacting the compound 2-bromotanshinone I with 3,4-dimethylboric acid.

LC-MS: retention time: 3.60 min (98.2%), m/z: 381.0 (M+H).

BS-TA-07 is prepared according to the process for BS-TA-03 using the same reagents as above by reacting the compound 2-bromotanshinone I with 2-methoxy-phenylboric acid.

LC-MS: retention time: 3.30 min (98.51%), m/z: 383.0 (M+H).

BS-TA-09 is prepared according to the process for BS-TA-03 using the same reagents as above by reacting the compound 2-bromotanshinone I with 2-methoxypyridyl-3-boric acid.

LC-MS: retention time: 3.20 min (98.82%), m/z: 384.0 (M+H).

BS-TA-14 is prepared according to the process for BS-TA-03 using the same reagents as above by reacting the compound 2-bromotanshinone I with ethylboric acid.

LC-MS: retention time: 3.20 min (94.36%), m/z: 305.2 (M+H).

BS-TA-41 is prepared according to the process for BS-TA-03 using the same reagents as above by reacting the compound 2-bromotanshinone I with 3-pyridylboric acid.

LC-MS: retention time: 2.80 min (98.75%), m/z: 354.0 (M+H).

EXAMPLE 2

Synthesis of Compound BS-TA-31

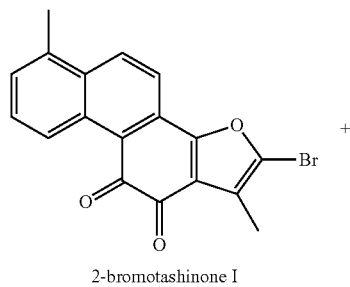
2-bromotashinone I

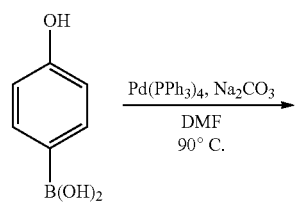

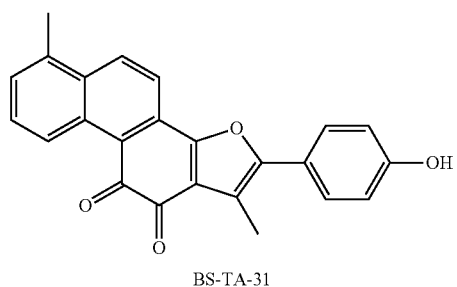
BS-TA-31

Under nitrogen protection, 2-bromotanshinone I (1.2 g, 3.4 mmol), 4-hydroxyphenylboric acid (2.4g, 17.0 mmol) and sodium carbonate (2.1 g, 20.3 mmol) are added to N,N-dimethylformamide (50 mL), and then tetra(triphenylphosphine)palladium (781 mg, 0.7 mmol) is added. After the reaction solution is heated up to 90° C. and stirred for 16 hours, water (200 mL) is added to the reaction mixture. Dichloromethane (100 mL*4) is used for extraction. The organic phase is washed with saturated solution of sodium bicarbonate (200 mL*4) and dried with anhydrous sodium sulfate. The crude product resulted from concentration is washed with ethanol to give the compound BS-TA-31(800 mg, yield 58%) as a brown solid.

EXAMPLE 3

Synthesis of Compound BS-TA-301

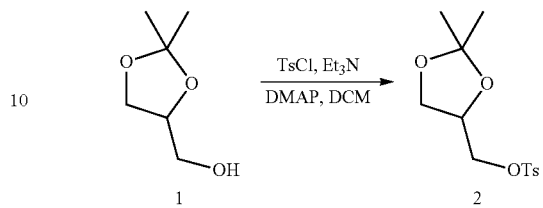

wherein, TsCl represents p-toluenesulfonyl chloride; Et₃N represents triethylamine; and DMAP represents 4-dimethylaminopyridine.

At 0° C., triethylamine (1.1 g, 11.3 mmol), p-toluenesulfonyl chloride (1.5 g, 7.9 mmol) and 4-dimethylaminopyridine (185 mg, 1 5 mmol) are added into dichloromethane (20 mL) in which the compound 1 (1 g, 7.6 mmol) is dissolved. After the reaction solution is stirred for 12 hours at room temperature, dichloromethane (100 mL) and water (20 mL) are added for dilution. 1N hydrochloric acid is used to adjust the pH to 3. Dichloromethane (50 mL*3) is used for extraction. The organic phases are combined, dried with anhydrous sodium sulfate, and concentrated to give the compound 2 (2g, yield 95%).

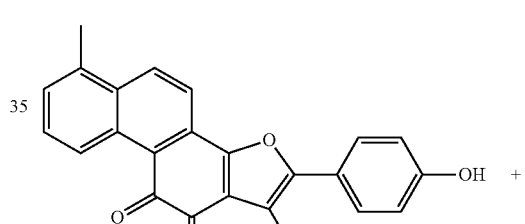
BS-TA-31

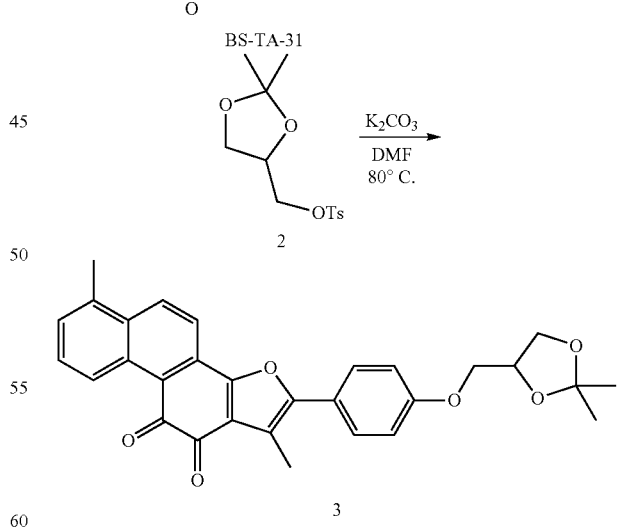

Potassium carbonate (141 mg, 1.0 mmol) and compound 2 (140 mg, 0.5 mmol) are added into N,N-dimethylformamide (2 mL) in which BS-TA-31 (150 mg, 0.4 mmol) is dissolved. The reaction solution is heated up to 80° C. and stirred for 24 hours. When the reaction is completed, dichloromethane (100 mL) is added for extraction. The organic phase is washed with water (50 mL*4), dried with anhydrous sodium sulfate, and concentrated to give the compound 3 (200 mg, yield 100%). This crude product is directly applied to the next step of reaction without purification.

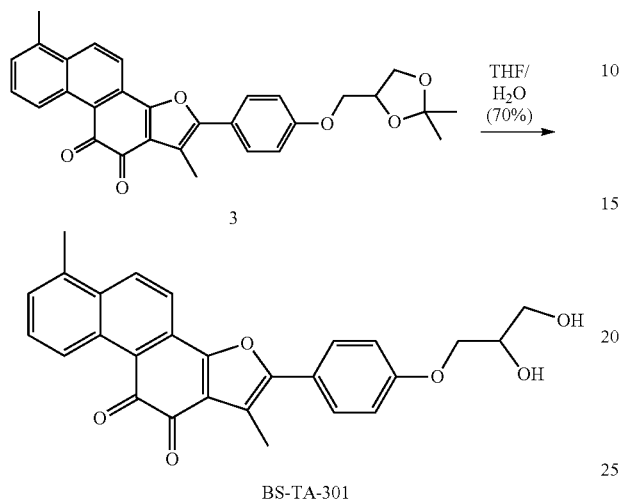

Tetrahydrofuran/water (70% V/V) (2 mL) is added dropwise into a dichloromethane (40 mL) solution in which the compound 3 (200 mg, 0.4 mmol) is dissolved. The reaction solution is heated up to 45° C. and stirred for 1 hour, and then cooled down to room temperature. Water (10 mL) is added to the reaction solution and dichloromethane (50 mL*4) is used for extraction. The organic phases are combined, dried with anhydrous sodium sulfate, and concentrated to give a crude product, which is then washed with ethanol to give the compound BS-TA-301 (73 mg, yield 50%) as a brown solid.

LC-MS: retention time: 1.93 min (92.7%); m/z: 443.2 (M+H).

$^1$H NMR (300 Hz, DMSO d-$_6$) δ 9.123 (d, 1H), 8.375 (d, 1H), 7.928 (d, 1H), 7.706 (d, 2H), 7.557 (m, 1H), 7.386 (d, 1H), 7.112 (d, 2H), 5.016 (d, 1H), 4.722 (m, 1H), 4.096 (m, 1H), 3.952 (m, 1H), 3.841 (m, 1H), 3.489 (m, 2H), 2.636 (s, 3H), 2.401(s, 3H).

EXAMPLE 4

Synthesis of Compound BS-TA-32

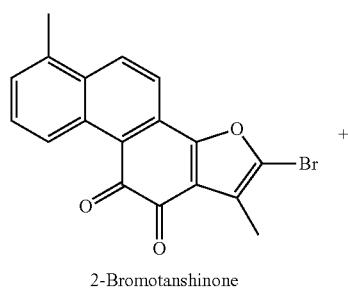

2-Bromotanshinone

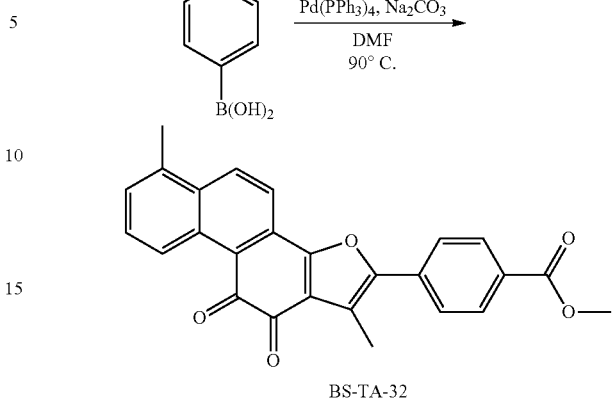

To N,N-dimethylformamide (10 mL) are added 2-bromotanshinone I (200 mg, 0.56 mmol), 4-methoxycarbonylphenylboric acid (507 mg, 2.8 mmol) and sodium carbonate (358 mg, 3.4 mmol). Then under nitrogen protection, tetra (triphenylphosphine)palladium (65 mg, 0.056 mmol) is added. The reaction solution is heated up to 90° C. and stirred for 16 hours. When the reaction is completed, water (100 mL) is added to the reaction solution and dichloromethane (50 mL*4) is used for extraction. The organic phases are combined, washed with anhydrous sodium bicarbonate (100 mL*4), dried with anhydrous sodium sulfate, and concentrated to give a crude product, which is then purified and separated with a silica-gel chromatography column to give the compound BS-TA-32 (140 mg, yield 61%) as a brown solid.

EXAMPLE 5

Synthesis of Compound BS-TA-302

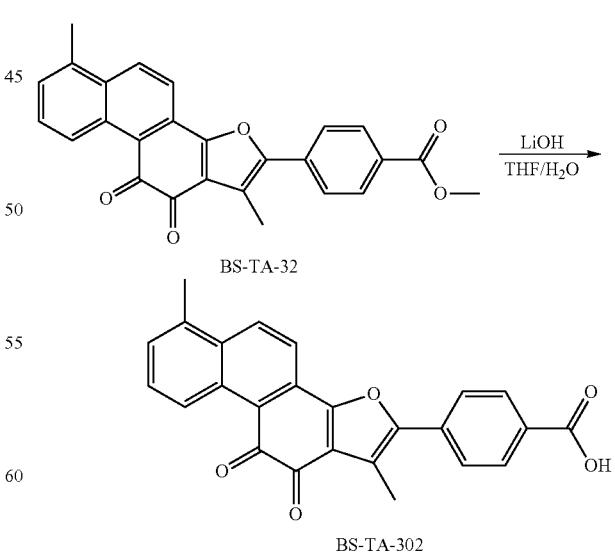

wherein, LiOH represents lithium hydroxide.

To a mixed solution of N,N-dimethylformamide (20 mL) and water (4 mL) is added BS-TA-32 (100 mg, 0.24 mmol), followed by the addition of lithium hydroxide (40 mg, 0.96 mmol). The reaction solution is stirred for 18 hours at room temperature. The solvent N,N-dimethylformamide is removed after the reaction is completed. The reaction solution is adjusted with trifluoroacetic acid/water (70%) to pH 3-4, and the solid resulted from filtration is washed with ethanol to give the compound BS-TA-302 (37 mg, yield 37%) as a brown solid.

LC-MS: retention time: 1.657 min; m/z: 397 (M+H);

$^1$H NMR (300 Hz, DMSO d-$_6$) δ 13.153 (s, 1H), 8.172-7.916 (m, 5H), 7.804 (d, 2H), 7.535 (m, 2H), 2.716 (s, 3H), 2.553 (s, 3H).

EXAMPLE 6

Synthesis of Compound BS-TA-306

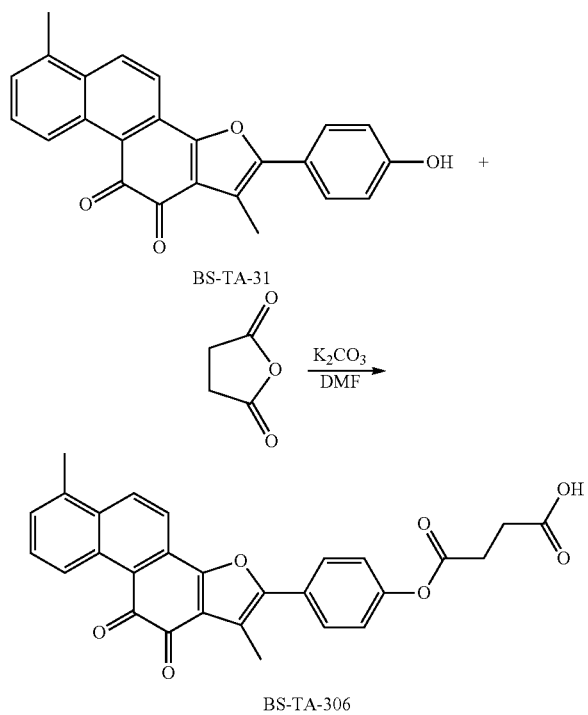

To N,N-dimethylformamide (2 mL) is added BS-TA-31 (50 mg, 0.14 mmol), followed by potassium carbonate (56 mg, 0.41 mmol) and succinic anhydride (15 mg, 0.15 mmol). The reaction solution is stirred overnight at room temperature. After the reaction is completed, water (10 mL) is added and dichloromethane (20 mL*3) is used for extraction. The organic phases are combined, washed with water, dried with anhydrous sodium sulfate, and concentrated to give a crude product, which is then purified and separated via preparative thin layer chromatography to give the compound BS-TA-306 (30 mg, yield 48%) as a brown solid.

LC-MS: retention time: 1.547min; m/z: 469 (M+H);

$^1$H NMR (300 Hz, DMSO d-$_6$) δ 9.997 (s, 1H), 8.758 (d, 1H), 8.449 (m, 1H), 7.919 (m, 1H), 7.642-7.519 (m, 3H), 7.423 (m, 1H), 6.952-6.907 (m, 2H), 3.869 (m, 1H), 3.685 (m, 1H), 2.904 (m, 1H), 2.730 (s, 3H), 2.174 (s, 3H), 1.229 (s, 2H), 0.850 (m, 1H).

EXAMPLE 7

Synthesis of Compound BS-TA-307

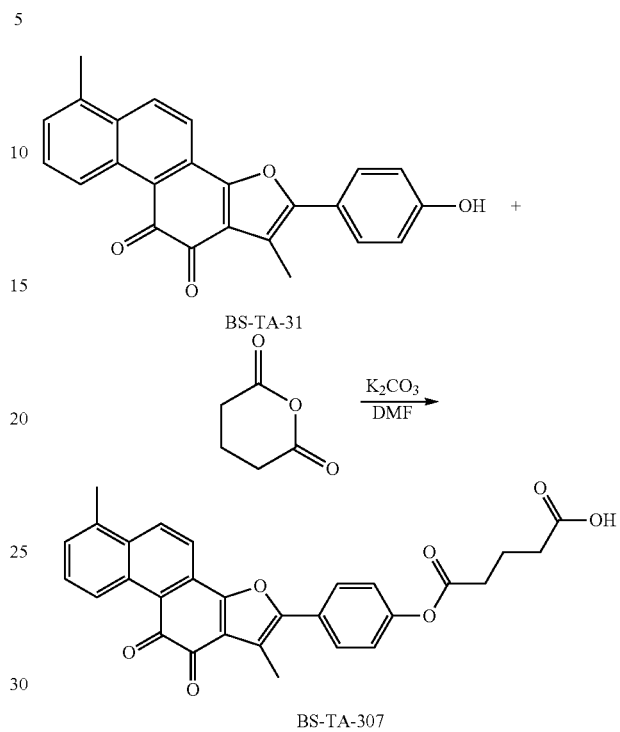

To N,N-dimethylformamide (2 mL) is added BS-TA-31 (70 mg, 0.20 mmol), followed by potassium carbonate (79 mg, 0.57 mmol) and glutaric anhydride (33 mg, 0.29 mmol). The reaction solution is stirred overnight at room temperature. After the reaction is completed, water (10 mL) is added and dichloromethane (20 mL*3) is used for extraction. The organic phases are combined, washed with water, dried with anhydrous sodium sulfate, and concentrated to give a crude product, which is then purified and separated via preparative thin layer chromatography to give the compound BS-TA-307 (25 mg, yield 28%) as a red solid.

LC-MS: retention time: 1.530min; m/z: 483 (M+H);

$^1$H NMR (300 Hz, DMSO d-$_6$) δ 9.989 (s, 1H), 8.533-8.423 (dd, 2H), 7.880 (m, 1H), 7.636-7.532 (m, 3H), 7.414 (d, 1H), 6.925 (d, 2H), 3.156-3.132 (m, 1H), 2.905-2.876 (m, 2H), 2.726-2.685 (m, 4H), 2.233 (s, 3H), 1.991 (m, 1H), 1.905 (m, 1H).

EXAMPLE 8

Synthesis of Compound BS-TA-309

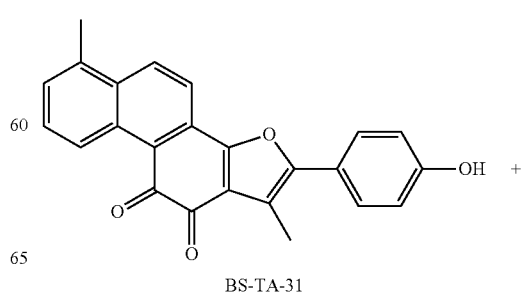

-continued

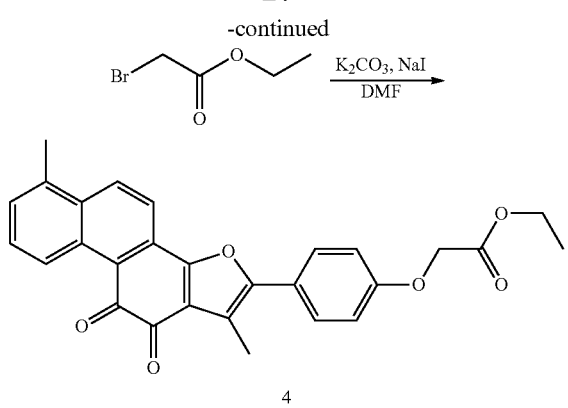

To N,N-dimethylformamide (2 mL) is added BS-TA-31 (100 mg, 0.27 mmol), followed by potassium carbonate (113 mg, 0.82 mmol), ethyl bromoacetate (68 mg, 0.41 mmol) and sodium iodide (65 mg, 0.43 mmol). The reaction solution is heated up to 80° C. and stirred for 24 hours. After the reaction is completed, dichloromethane (100 mL) is added to the reaction solution. The crude product resulted from washing with water, drying and concentrating is directly applied to the next step of reaction without purification.

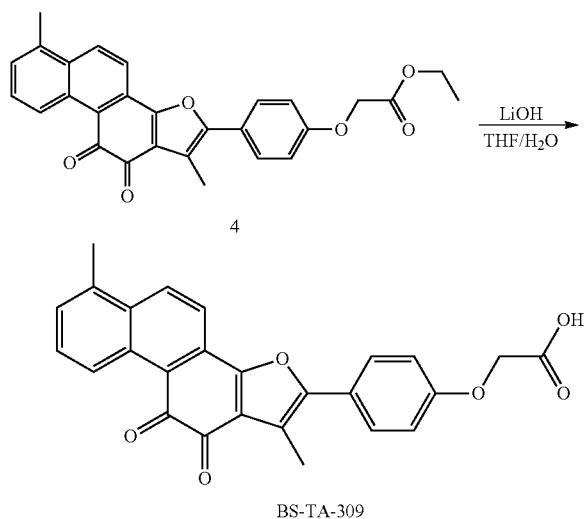

To a mixed solution of N,N-dimethylformamide (20 mL) and water (4 mL) is added the compound 4 (120 mg, 0.26 mmol), followed by lithium hydroxide (44 mg, 1.1 mmol). The reaction solution is stirred for 18 hours at room temperature. The solvent N,N-dimethylformamide is removed after the reaction is completed. The reaction solution is adjusted with trifluoroacetic acid/water (70%) to pH 3-4, and the solid resulted from filtration is washed with ethanol to give the compound BS-TA-309 (40 mg, yield 37%) as a brown solid.

LC-MS: retention time: 1.578min; m/z: 427 (M+H);

$^1$H NMR (300 Hz, DMSO d-$_6$) δ 9.147 (d, 1H), 8.427 (d, 1H), 7.986 (d, 1H), 7.722 (d, 3H), 7.419 (d, 1H), 7.064 (d, 2H), 4.638 (s, 2H), 2.720 (s, 2H), 2.386 (s, 3H).

EXAMPLE 9

Evaluation of the 2-alkyl- or 2-aromatic-substituted tanshinone I Derivatives of the Present Invention for their Anti-Leukemia Activities (1) Experimental Materials Leukemia cell lines: K562/adr (drug-resistant, chronic myeloid leukemia, CML), NB4 (acute promyelocytic leukemia, AML), Kasumi-1 (acute myeloid leukemia M2 type, AML-M2), Jurkat (acute lymphoblastic leukemia, ALL), all of which are donated by Cancer Research Institute of Zhejiang University, China; and H9 (acute lymphoblastic leukemia, ALL), which is purchased from China Center for Type Culture Collection (CCTCC).

Reagents: The standard sample of tanshinone I (TA) is purchased from Chengdu Mansite Pharmaceutical Co., Ltd., Sichuan, China, and the 2-alkyl- or 2-aromatic-substituted tanshinone I derivatives are prepared according to the present invention.

Main apparatuses: a Thermo Scientific 3111 incubator and a Bio-Rad iMark microplate absorbance reader.

(2) Experimental Method

The standard sample of tanshinone I (TA) and the 2-alkyl- or 2-aromatic-substituted tanshinone I derivatives of the present invention are sufficiently dissolved in dimethylsulfoxide to produce a stock solution of 10 mg/mL, which is refrigerated at 4° C. and stored in dark, and is diluted with cell culture medium to a desired concentration prior to experimentation.

Obtaining 6000 well-growing leukemia cells and inoculating them into wells of a 96-well cell culture plate. The culture medium is the RPMI-1640 cell culture medium containing 10% fetal bovine serum. After adding on the second day the 2-alkyl- or 2-aromatic-substituted tanshinone I derivatives of different concentrations and mixing uniformly, placing the plate in a carbon dioxide cell incubator (5% $CO_2$) at 37° C. and incubated for 72 hours. Then the viable cell concentration is determined by MTT method. In this experiment, the cell viability in control group (not treated with any compound) is set as 100%, and the cell viability (%) after treatment by the compounds and the half maximum inhibitory concentration for the leukemia cell at 72 hours ($IC_{50}$ value of 72 hours, μg/mL) are calculated.

(3) The Experimental Results

The experimental results are shown in table 1.

Table 1 shows that the 2-alkyl- or 2-aromatic-substituted tanshinone I derivatives of the present invention can induce death of most leukemia cells. As compared with tanshinone I per se, the inventive 2-alkyl- or 2-aromatic-substituted tanshinone I derivatives BS-TA-302 improves the anti-NB4 (acute promyelocytic leukemia) activity and the anti-H9 (acute lymphoblastic leukemia) activity by almost 5-fold; BS-TA-301 improves the anti-Jurkat (acute lymphoblastic leukemia) activity by more than 3-fold.

TABLE 1

Determination of the inhibiting concentrations of the 2-alkyl- or 2-aromatic-substituted tanshinone I derivatives on leukemia cell growth (72 h, $IC_{50}$ (μg/mL) value and $IC_{90}$ (μg/mL) value).

| Compounds | K562/ADR | | Kasumi-1 | | NB4 | | Jurkat | | H9 | |
|---|---|---|---|---|---|---|---|---|---|---|
| | $IC_{50}$ | $IC_{90}$ | $IC_{50}$ | $IC_{90}$ | $IC_{50}$ | $IC_{90}$ | $IC_{50}$ | $IC_{90}$ | $IC_{50}$ | $IC_{90}$ |
| TA | 0.88 | 4.17 | 0.99 | 3.62 | 0.98 | 2.5 | 1.74 | 8.42 | 3.5 | 13.06 |
| BS-TA-03 | 8.84 | 28.66 | 9.66 | 30.3 | 1.13 | 3.64 | 1.88 | 6.97 | 6.4 | >16 |
| BS-TA-04 | 15.5 | >16 | >16 | >16 | 4.09 | 11.2 | 4.83 | 9.72 | 6.7 | >16 |
| BS-TA-301 | 1.36 | 7.61 | 0.97 | 31.1 | 0.31 | 3.22 | 0.48 | >16 | 3 | >16 |
| BS-TA-302 | 1.08 | 3.6 | 3.85 | 17.5 | 0.2 | 1 | 0.84 | >16 | 0.7 | 1.98 |

EXAMPLE 10

Evaluation of the Anti-Human Multiple Myeloma Cell Activities by the 2-alkyl- or 2-aromatic-substituted tanshinone I Derivatives of the Present Invention (1) Experimental Materials Multiple myeloma cell lines: RPMI8226 (multiple myeloma), purchased from Fuxiang Bio-tech Co. Ltd., Shanghai, China.

Reagents: the same as in Example 9.

Main apparatuses: a Thermo Scientific 3111 incubator and a Bio-Rad iMark microplate reader.

(2) Experimental Method

The standard sample of tanshinone I (TA) and the 2-alkyl- or 2-aromatic-substituted tanshinone I derivatives of the present invention are sufficiently dissolved in dimethylsulfoxide to produce a stock solution of 10 mg/mL, which is refrigerated at 4° C. and stored in dark, and is diluted with cell culture medium to a desired concentration prior to experimentation.

Obtaining 6000 well-growing leukemia cells and inoculating them into wells of a 96-well cell culture plate. The culture medium is the RPMI-1640 cell culture medium containing 10% fetal bovine serum. After adding on the second day the 2-alkyl- or 2-aromatic-substituted tanshinone I derivatives of different concentrations and mixing uniformly, placing the plate in a carbon dioxide cell incubator (5% $CO_2$) at 37° C. and incubated for 72 hours. Then the viable cell concentration is determined by MTT method. In this experiment, the cell viability in control group (not treated with any compound) is set as 100%, and the cell viability (%) after treatment by the compounds and the half maximum inhibitory concentration for the leukemia cell at 72 hours ($IC_{50}$ value of 72 hours, μg/mL) are calculated.

(3) The Experimental Results

The experimental results are shown in table 2.

Table 2 shows that, as compared with tanshinone I per se, the tanshinone I derivative of the present invention BS-TA-301 improves the anti-RPMI8226 cell line activity significantly and is effective in inducing the death of human myeloma cells and inhibiting the growth of the tumor cells.

EXAMPLE 11

Evaluation of Anti-human Solid Tumor Effect of the 2-alkyl- or 2-aromatic-substituted tanshinone I Derivatives of the Present Invention (1) Experimental Materials Human solid tumor cell lines:

Hep-2 (laryngeal carcinoma), A549 (human lung cancer), CaES-17 (esophageal cancer cell), PC-3 (prostate cancer), CNE (nasopharyngeal carcinoma cell), and SK-OV-3 (ovarian cancer cell), all of which are purchased from China Center For Type Culture Collection; RKO (human colon adenocarcinoma cell), MGC 803 (human gastric cancer cell), MG63 (osteosarcoma) and U87 MG (malignant glioma cell), all of which are purchased from Fuxiang Bio-tech Co. Ltd., Shanghai, China; PANC-1 (pancreatic cancer), Becap37 (human breast cancer cell), Hela (human cervical cancer cell) and Hep G2 (human liver cancer cell), all of which are donated by Cancer Research Institute of Zhejiang University, China.

Reagents: the same as in Example 9.

Main apparatuses: a Thermo Scientific 3111 incubator and a Bio-Rad iMark microplate reader.

(2) Experimental Method

The standard sample of tanshinone I (TA) and the 2-alkyl- or 2-aromatic-substituted tanshinone I derivatives of the present invention are sufficiently dissolved in dimethylsulfoxide to produce a stock solution of 10 mg/mL, which is refrigerated at 4° C. and stored in dark, and is diluted with a cell culture medium to the desired concentration prior to experimentation.

Obtaining 6000 well-growing human solid tumor cells and inoculating them into wells of a 96-well cell culture plate. The culture medium is DMEM High Glucose cell culture medium containing 10% fetal bovine serum. The plate is placed in a carbon dioxide cell incubator (5% $CO_2$) at 37° C. and incubated for 24 hours. After adding the 2-alkyl- or 2-aromatic-substituted tanshinone I derivatives of different concentrations and mixing uniformly, the plate is placed in a carbon dioxide cell incubator (5% $CO_2$) at 37° C. and incubated for 72 hours. Then the viable cell concentration is determined by MTT method. In this experiment, the cell viability in control group (not treated with any compound) is set as 100%, and the cell viability (%) after treatment by the compounds and the half maximum inhibitory concentration for the leukemia cell at 72 hours ($IC_{50}$ value of 72 hours, μg/mL) are calculated.

(3) Experimental Results

The experimental results are shown in Table 2.

Table 2 shows that the 2-alkyl- or 2-aromatic-substituted tanshinone I derivatives of the present invention can, to a certain extent, induce the death of human solid tumor cells and inhibit the growth of these tumor cells. The 2-alkyl-substituted tanshinone I derivatives of the present invention BS-TA-301 and BS-TA-302 show particularly remarkable effects and both exhibit broad-spectrum antitumor activity and are superior to that of tanshinone I per se in terms of anti-Becap37 (human breast cancer cell), anti-Hela (human cervical cancer cell), anti-Hep G2 (human liver cancer cell), anti-RKO (human colon adenocarcinoma cell), anti-U87 MG (malignant glioma cell) and anti-SK-OV-3 (ovarian cancer cell) cell lines. In addition, BS-TA-301 also exhibits good antitumor activity in anti-CNE (nasopharyngeal carcinoma cell). As compared with tanshinone I per se, BS-TA-302 significantly improves both the anti-MGC 803 (human gastric cancer cell) activity and the anti-PC-3 (prostate cancer) activity. BS-TA-03 also exhibits good activity in anti-RKO (human colon adenocarcinoma cell), anti-CNE (nasopharyngeal carcinoma cell) and anti-PC-3 (prostate cancer) cell lines. BS-TA-04 also exhibits anti-U87 MG (malignant glioma cell) cell line activity that is superior to that of tanshinone I per se.

TABLE 2

Determination of the inhibiting concentrations of the 2-alkyl- or 2-aromatic-substituted tanshinone I derivatives on human solid tumor cell growth (72 h, $IC_{50}$ (μg/mL) value and $IC_{90}$ (μg/mL) value).

| Compounds | RPMI 8226 | | A549 | | PANC-1 | |
|---|---|---|---|---|---|---|
| | $IC_{50}$ | $IC_{90}$ | $IC_{50}$ | $IC_{90}$ | $IC_{50}$ | $IC_{90}$ |
| TA | 0.96 | 10.86 | 4.03 | 17.29 | 2.7 | >16 |
| BS-TA-03 | 2 | 16.49 | 6.45 | >16 | 3.46 | >16 |
| BS-TA-04 | 4 | 16.06 | 6.92 | >16 | 9.8 | >16 |
| BS-TA-301 | 0.58 | 16.2 | 6.68 | 25.9 | 7.34 | 24.1 |
| BS-TA-302 | 1 | 16.56 | 16.59 | >16 | 5.48 | >16 |

| Compounds | Becap-37 | | MG-63 | | Hep G2 | | RKO | |
|---|---|---|---|---|---|---|---|---|
| | $IC_{50}$ | $IC_{90}$ | $IC_{50}$ | $IC_{90}$ | $IC_{50}$ | $IC_{90}$ | $IC_{50}$ | $IC_{90}$ |
| TA | 3.03 | >16 | 0.96 | >16 | 2.19 | 22.13 | 1.83 | >16 |
| BS-TA-03 | 3.96 | >16 | 3.18 | >16 | 5.48 | >16 | 1.35 | >16 |
| BS-TA-04 | 9.34 | >16 | 10.33 | >16 | 14.46 | >16 | 5.01 | >16 |
| BS-TA-301 | 1.99 | 7.83 | 1.62 | 7.44 | 2.09 | 16.33 | 0.87 | 26.57 |
| BS-TA-302 | 1.28 | >16 | 1.05 | >16 | 1.94 | >16 | 1.53 | >16 |

| Compounds | U87-MG | | Hela | | CaEs-17 | | CNE | |
|---|---|---|---|---|---|---|---|---|
| | $IC_{50}$ | $IC_{90}$ | $IC_{50}$ | $IC_{90}$ | $IC_{50}$ | $IC_{90}$ | $IC_{50}$ | $IC_{90}$ |
| TA | 6.36 | 14.63 | 4 | >16 | 3.18 | 16.00 | 7.4 | >16 |
| BS-TA-03 | 6.63 | 16.76 | 4 | >16 | 5.19 | 20.41 | 3.9 | 97 |
| BS-TA-04 | 5.73 | 19.19 | 5.5 | 22.22 | 11.04 | 28.82 | 10.5 | >16 |
| BS-TA-301 | 2.85 | 15.45 | 1.07 | 24.03 | 3.78 | >16 | 3.2 | 45 |
| BS-TA-302 | 0.5 | >16 | 0.5 | 16 | 6.83 | >16 | 15 | >16 |

| Compounds | Hep-2 | | MGC-803 | | PC-3 | | SK-OV-3 | |
|---|---|---|---|---|---|---|---|---|
| | $IC_{50}$ | $IC_{90}$ | $IC_{50}$ | $IC_{90}$ | $IC_{50}$ | $IC_{90}$ | $IC_{50}$ | $IC_{90}$ |
| TA | 3.15 | >16 | 1.62 | 9.26 | 6.63 | 10.57 | >16 | >16 |
| BS-TA-03 | 9.17 | >16 | 4.65 | 18.4 | 4.99 | 17.5 | >16 | >16 |
| BS-TA-04 | 11.64 | >16 | 8.88 | 23.93 | >16 | >16 | >16 | >16 |
| BS-TA-301 | 5.27 | >16 | 1.74 | 16 | 9.94 | >16 | 11.73 | >16 |
| BS-TA-302 | 8 | >16 | 0.38 | 3.3 | 6.49 | >16 | 11.1 | >16 |

The invention claimed is:

1. A process for preparing a compound of formula (I):

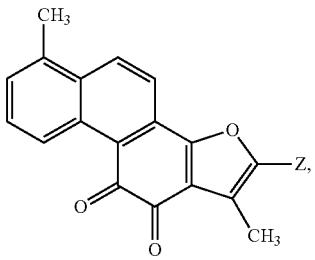

or a pharmaceutically acceptable salt thereof;
wherein
Z is selected from the group consisting of R, Ar or Het;
R is selected from substituted or unsubstituted $C_1$-$C_{18}$ alkyl, substituted or unsubstituted $C_2$-$C_{18}$ alkenyl or alkynyl, and substituted or unsubstituted $C_3$-$C_7$ cycloalkyl or cycloalkenyl, wherein R is not a carboxyl-substituted $C_1$-$C_{18}$ alkyl, a carboxyl-substituted $C_2$-$C_{18}$ alkenyl, or a methyl substituted with an amino or a substituted amino;
Ar is selected from substituted or unsubstituted aryl;
Het is selected from substituted or unsubstituted heteroaryl or heterocyclyl;
each of the aforementioned substituted groups is substituted by one or more substituents selected from the group consisting of halogen, amino, $C_1$-$C_6$ alkyl-substituted amino, nitro, cyano, $C_1$-$C_6$ alkoxy, thiol, $C_1$-$C_6$ alkylthio, and a water soluble functional group selected from the group consisting of polyhydroxy alkoxy, saccharide residue, carboxyl, sulfonic acid group, phosphate group, polyhydroxy alkoxy carbonyl, carboxyl alkoxy, and carboxyl alkyl formyloxy, wherein the alkoxy and alkyl in the aforementioned water soluble functional groups have 1-8 carbon atoms, respectively; and
Ar may further be substituted with $C_1$-$C_6$ alkyl;
comprising firstly subjecting tanshinone I,

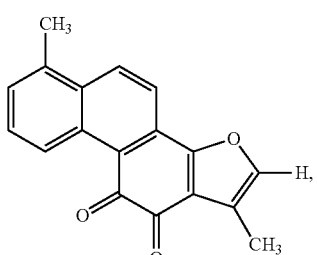

Tanshinone I to bromination to produce a 2-bromotanshinone I intermediate,

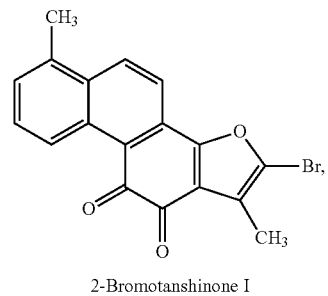 [SMILES: Cc1c(Br)oc2c1C(=O)C(=O)c1c-2ccc2c(C)cccc12]

2-Bromotanshinone I then subjecting said intermediate to a C-C bond formation reaction with corresponding organic boric acid or borate in the presence of a catalyst to produce the compound of formula (I).

2. A method for treating a tumor, comprising administering to a subject in need thereof an effective amount of a compound of formula (I):

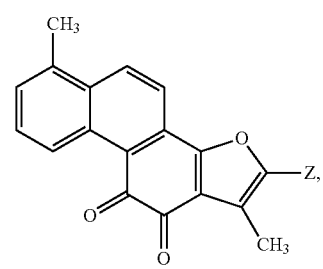

or a pharmaceutically acceptable salt thereof;
wherein
Z is selected from the group consisting of R, Ar or Het;
R is selected from substituted or unsubstituted $C_1$-$C_{18}$ alkyl, substituted or unsubstituted $C_2$-$C_{18}$ alkenyl or alkynyl, and substituted or unsubstituted $C_3$-$C_7$ cycloalkyl or cycloalkenyl, wherein R is not a carboxyl-substituted $C_1$-$C_{18}$ alkyl, a carboxyl-substituted $C_2$-$C_{18}$ alkenyl, or a methyl substituted with an amino or a substituted amino;
Ar is selected from substituted or unsubstituted aryl;
Het is selected from substituted or unsubstituted heteroaryl or heterocyclyl;
each of the aforementioned substituted groups is substituted by one or more substituents selected from the group consisting of halogen, amino, $C_1$-$C_6$ alkyl-substituted amino, nitro, cyano, $C_1$-$C_6$ alkoxy, thiol, $C_1$-$C_6$ alkylthio, and a water soluble functional group selected from the group consisting of polyhydroxy alkoxy, saccharide residue, carboxyl, sulfonic acid group, phosphate group, polyhydroxy alkoxy carbonyl, carboxyl alkoxy, and carboxyl alkyl formyloxy, wherein the alkoxy and alkyl in the aforementioned water soluble functional groups have 1-8 carbon atoms, respectively; and
Ar may further be substituted with $C_1$-$C_6$ alkyl;
wherein said treating refers to causing regression of the tumor.

3. The method of claim 2, wherein the tumor is selected from the group consisting of leukemia, multiple myeloma, lymphoma, liver cancer, gastric cancer, breast cancer, cholangiocellular carcinoma, pancreatic cancer, lung cancer, colorectal cancer, osteosarcoma, human cervical cancer, glioma, nasopharyngeal carcinoma, laryngeal carcinoma, esophageal cancer, middle ear tumor, melanoma and prostate cancer.

* * * * *